United States Patent [19]
Tonokura

[11] Patent Number: 5,564,425
[45] Date of Patent: Oct. 15, 1996

[54] CATHETER WITH BUILT-IN-DISPLAY

[75] Inventor: Eiji Tonokura, Tokyo, Japan

[73] Assignee: Tonokura Ika Kogyo K.K., Japan

[21] Appl. No.: 295,376

[22] Filed: Aug. 24, 1994

[30] Foreign Application Priority Data

Aug. 24, 1993 [JP] Japan ................ 5-050455 U

[51] Int. Cl.$^6$ ................................................ A61B 5/00
[52] U.S. Cl. .................... 128/673; 128/691; 128/692; 128/748; 604/93; 604/264
[58] Field of Search ................ 128/772, 662.06, 128/736, 691, 692, 748, 673; 604/93, 118, 181, 186, 207, 264, 280, 97, 98

[56] References Cited

U.S. PATENT DOCUMENTS

| | | | |
|---|---|---|---|
| 3,669,094 | 6/1972 | Heyer | 128/2 |
| 4,114,603 | 9/1978 | Wilkinson | 128/2 R |
| 4,608,996 | 9/1986 | Brown | 128/760 |
| 4,994,035 | 2/1991 | Mokros | 604/118 |
| 5,135,488 | 8/1992 | Foote et al. | 604/97 |
| 5,279,563 | 1/1994 | Brucker et al. | 604/98 |

*Primary Examiner*—Corrine M. McDermott
*Assistant Examiner*—N. Kent Gring
*Attorney, Agent, or Firm*—Sixbey, Friedman, Leedom & Ferguson, P.C.; Gerald J. Ferguson, Jr.; David S. Safran

[57] ABSTRACT

The catheter for supplying fluids to or draining them from the body of a patient is provided in its tube wall with a detector device integrated in the form of a block unit. The detector device is constituted by a first sensor for sensing a first status, e.g. pressure, of the fluid, a second sensor for sensing a second status, e.g. temperature thereof, a first display device for displaying the first status sensed by the first sensor, and a second display device for displaying the second status sensed by the second sensor. The signals indicative of the first status, e.g. pressure, sensed by the first sensor are processed by a first control unit and displayed on the first display device and the signals indicative of the second status, e.g. temperature, sensed by the second sensor are processed by a second control unit and displayed on the second display device. The first and second display devices are disposed on the base end side of the catheter so as to be exposed to the outside of the tube of the catheter in order to allow the operator to visually monitor the data sensed by the first and second sensors and displayed on the first and second display devices from the body of a patient into which the catheter is inserted.

7 Claims, 2 Drawing Sheets

CATHETER WITH BUILT-IN-DISPLAY

BACKGROUND OF THE INVENTION

1. Field of the Invention

The present invention relates to a catheter and, more particularly, to a catheter or a cannula for use in the therapy field, especially for surgery of the organ such as heart of a patient, which is so adapted as to be inserted into the body of the patient for supplying fluids such as blood, medicine or the like into the body or for draining fluids from the body.

2. Description of the Related Art

In the medical field, a variety of catheters are being employed for various surgery including the heart surgery and for various examination. The catheter is so adapted as to supply blood or medicine or the like to the body of a patient or to drain fluids, such as blood, from the body by inserting the tip portion of its tube into a given location of the body through the blood vessel.

For or during examination or surgery, operators often demand to learn the temperature or pressure of fluids such as blood or medicine being supplied to the body of a patient or drained therefrom. Hitherto, for such purposes, there has been employed a pumping unit for supplying blood or medicinal fluids to the body of a patient under pressurized conditions or for sucking body fluids from the patient or a peripheral unit attached to the pumping unit and provided with a device for sensing the temperature and pressure of the fluids being supplied to or drained from the body of a patient. The temperature and pressure of the fluids are always being monitored through the devices by professional technicians or nurses and, in many occasions, the one monitoring the temperature and pressure verbally answers the operator to verbal demand from an operator to thereby let the operator or operators learn of the temperature and pressure of the fluids being supplied to the body or drained therefrom.

Such verbal communication, however, may cause operators inconvenience particularly during emergency surgery and it may impose unnecessary burdens upon the operators during surgery or examination. Further, it suffers from the disadvantage that the operator or operators may not be absorbed in operations or examination while monitoring the temperature and pressure of the fluid being supplied to or drained from the patient on a real-time basis.

SUMMARY OF THE INVENTION

Therefore, the present invention has the object to provide a catheter or a cannula so adapted as to allow an operator to immediately and directly learn the status, such as the temperature or pressure, of fluids, e.g. blood or medicine, being supplied to the body of a patient or drained therefrom, on a real-time basis.

In order to achieve the object, the present invention provides a catheter comprising:

a sensor disposed in a hollow tube of the catheter for sensing the status of a fluid passing through the hollow tube of the catheter; and a display device for displaying the status of the fluid sensed by the sensor, which is disposed at a location of a tube wall of the catheter so as to be always exposed to the outside of The tube wall thereof to be visually monitored at a location outside the body of a patient into which the catheter is inserted.

Given the structure as described hereinabove, the catheter further comprises a control unit for receiving input from the sensor and generating output to the display device, wherein the control unit is in the form of a block body or unit integral with the sensor and the display device so as for the display device to be exposed to the outside of the wall tube of the catheter and for the sensor to be exposed to the fluid passing through the hollow tube of the catheter and wherein the block member is embedded in the tube wall of the catheter so as for the display device to be monitered at a location outside the body of a patient.

The catheter according to this invention may be designed to sense at least one of the status, such as the temp or pressure, of the fluids to be supplied to or drained from the body of a patient and to display it on the display device.

In accordance with this invention, the catheter itself is provided with the functions of sensing the status of the fluids to be supplied to the body or drained therefrom and displaying it on the display device located outside the body, thereby allowing the operator to visually monitor the status of the fluids on the display device while manipulating the catheter. In particular, the status of the fluids sensed by the sensor and displayed on the display device of the catheter according to this invention reflects the conditions and states of the fluids immediately before or after being or having been supplied to the body or drained therefrom so that the operator can learn the accurate data of the fluids on a substantially real-time basis.

With the arrangement of the integral disposition of the control unit with the sensor and the display device, functional parts being employed for sensing the status of the fluids, such as blood or medicine, the block body or unit can be disposed integrally in the tube wall of the catheter according to this invention. This arrangement of the block body or unit presents the advantage that it can be prepared with ease.

Further, the sensor and the display device can be arranged in order to sense and display one of the status of the fluids, a data of the fluids being restricted to the one that the operator wishes to learn with highest priority.

The other objects, features and advantages of this invention will become apparent in the course of the description of this application which follows, with reference to the accompanying drawings.

DESCRIPTION OF THE PREFERRED EMBODIMENTS

The catheter according to this invention will be described in more detail by way of examples with reference to the accompanying drawings. It is to be noted herein that the embodiments will be described hereinafter only for the purpose of illustrations, not for the restrictive purposes in any respects.

Figure 1:
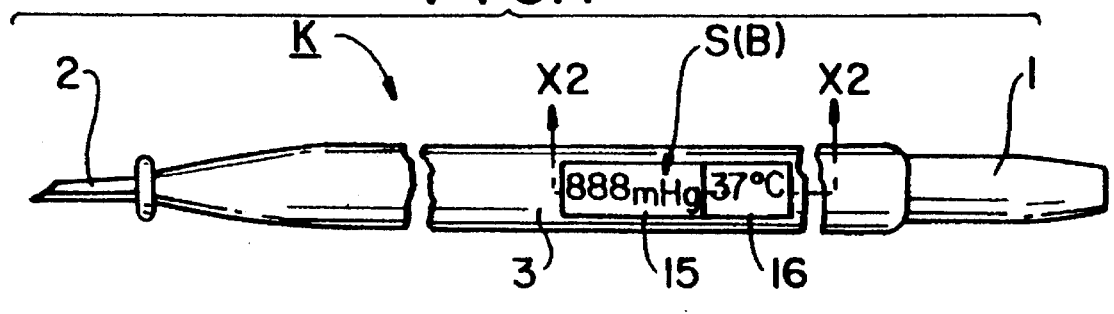
FIG. 1 is a top plan view showing a catheter according to the present invention.

As shown in FIG. 1, a catheter K designed for supplying fluids such as blood or medicine has a connection coupler 1 connected to its base end portion and a tube (not shown) extending from a pump (not shown) for supplying the fluids under pressure is connected to the connection coupler 1. A tip portion 2 of a flexible tube of the catheter K is directed and inserted into the body of a patient along and through its blood vessel up to its given position or location of the body at which or to which the fluids such as blood or medicine are supplied through the catheter K.

Figure 2:
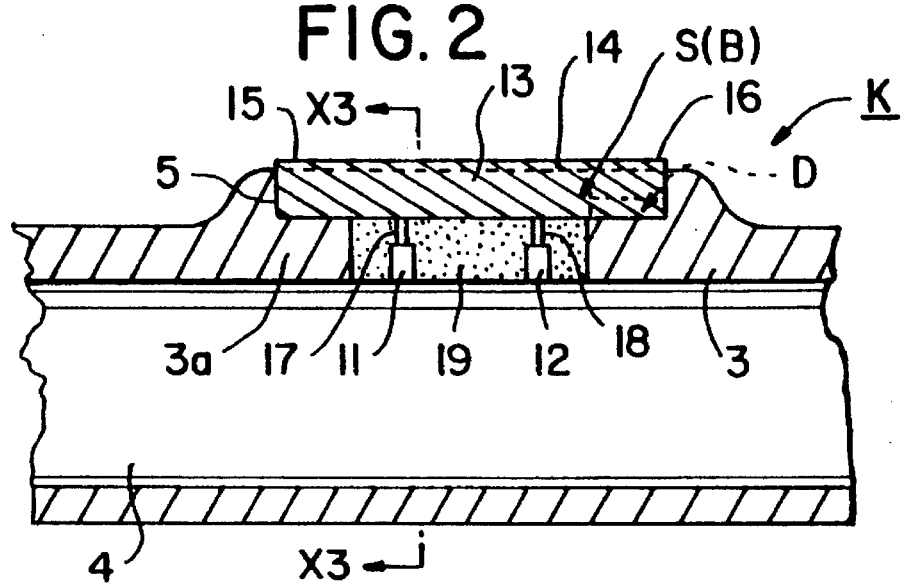
FIG. 2 is a partial side view in section showing an essential portion of the catheter according to the present invention, taken along line X2—X2 of FIG. 1.

As shown in FIG. 2, a detector unit S is disposed in a tube wall 3 of the catheter K at a location closer to the connection coupler 1. The detector unit S may comprise two sensors 11 and 12, two control units 13 and 14 as well as two display devices 15 and 16. The sensor 11 is so adapted as to sense the pressure of the fluids passing through the hollow passage of the catheter K which is inserted into the body of the patient. The signals sensed by the sensor 11 are output to the control unit 13 which in turn process the signals to thereby output signals indicative of the pressure of the fluids to the display device 15, as drive signals, in accordance with the pressure sensed, and the pressure sensed by the sensor 11 is displayed on the display device 15 (as shown in FIG. 1). Likewise, the sensor 12 is so adapted as to sense the temperature of the fluids to be supplied to or drained from the body of the patient into which the catheter K is inserted. The signals sensed by the sensor 12 are output to the control unit 14 which in turn process the signals to thereby output signals indicative of the temperature of the fluids to the display device 16, as drive signals, in accordance with the temperature sensed, and the temperature sensed by the sensor 12 is then displayed on the display device 16 (as shown in FIG. 1).

Each of the control units 13 and 14 may be constituted by an electric circuitry, such as an IC circuit, and they are integrally packaged in a block unit so as to be arranged in a lengthwise direction with the catheter K, i.e. along the course of the fluids passing through the hollow tube of the catheter K. The display devices 15 and 16 are integral with each other so as to be disposed on the outer surface sides of the respective control units 13 and 14. In the embodiment according to this invention, the display devices 15 and 16 are arranged of a liquid crystal display type, or of a digital display type, in the form of a thin plate or a sheet. The display devices 15 and 16 are integral with the respective control units 13 and 14 and exposed to the outside of the tube wall of the catheter K in order to visually monitor the displayed data from the outside. The sensors 11 and 12 are disposed underneath the respective control units 13 and 14 on the inner side of the tube wall 3 of the catheter K so as to be exposed to a fluid path 4 inside the catheter K through which the fluids are passing. The sensors 11 and 12 are connected with the control units 13 and 14 through lead wires 17 and 18, respectively, to transmit to the control units the signals sensed by the sensors.

As shown in FIG. 2, all the functional parts 11 to 18 may be integral together with each other in a block unit B. The sensors 11 and 12 are connected through the lead wires 17 and 18 to the integral unit in which the control units 13 and 14 are in turn integral with the display devices 15 and 16, respectively. The sensors 11 and 12 are embedded in a synthetic resin portion 19, together with the lead wires 17 and 18, so as to form a block unit. The block unit constituted by the control units 13 and 14 as well as the display devices 15 and 16 may be formed integrally with the block unit constituted by the synthetic resin portion 19 in which the sensors 11 and 12 as well as the lead wires 17 and 18 are embedded, thereby forming the integral block unit B. The synthetic resin portion 19 may be arranged in a form smaller than the block unit of the control units 13 and 14 integral with the display devices 15 and 16, respectively. In this case, the one side of the synthetic resin portion 19 to which the sensors are not exposed is attached to the one side of the block unit of the control units and the display devices, on which the control units are disposed, thereby forming a margin at the outer circumference of the lower side of the block unit around the synthetic resin portion.

The tube wall 3 of the catheter 1 is provided with a mounting aperture or hole 5 which in turn is arranged so as to allow the integral block unit B to be embedded or inserted into the tube wall 3 of the catheter K. The mounting aperture or hole 5 may be provided at its wall with a seat portion 3a. More specifically, the mounting aperture or hole 5 may be arranged such that its upper section above the seat portion 3a is larger in inner circumferential size than its lower section below the seat portion. Further, the upper section of the mounting aperture or hole 5 is arranged in order to fit the circumference of the block unit constituted by the control units 13 and 14 and the display devices 15 and 16, while the lower section thereof is in turn arranged in order to fit the circumference of the synthetic resin portion 19. In addition, the seat portion 3a of the mounting aperture or hole 5 is formed so as to seat the margin of the block unit. In other words, the integral block unit B is inserted or embedded into the mounting aperture or hole 5 and secured thereto. The block unit or member B may be secured integrally to the mounting aperture or hole 5 with adhesive or through a sealing member. In particular, when the sealing member is disposed around the circumferential wall of the aperture or hole 5, the integral block unit B can be inserted into the catheter K and, if needed, the block unit B may be detachable from the catheter K. In this case, the integral block unit B may be disposable after use.

The integral block unit B is disposed at a lengthwise location on the base end side of the catheter K in the vicinity of the connection coupler 1 or in the position apart from the connection coupler 1 by a given length closer to the other end side, in which the operator grips the catheter K for manipulation. In any event, the block unit B is arranged to be always exposed to the outside of the body of the patient in order to allow the operator to visually monitor the status of the fluids being supplied to or drained from the body of a patient, on a real time during operation.

With such a simple arrangement as described hereinabove, the catheter K according to this invention enables the operator to instantaneously and directly learn the status, such as the temperature and/or pressure, of the fluids passing through the fluid path 4 and supplied to the given location or drained therefrom, simply by visually monitoring the data displayed on the display devices 15 and 16 integrally incorporated in the catheter K.

Figure 4:
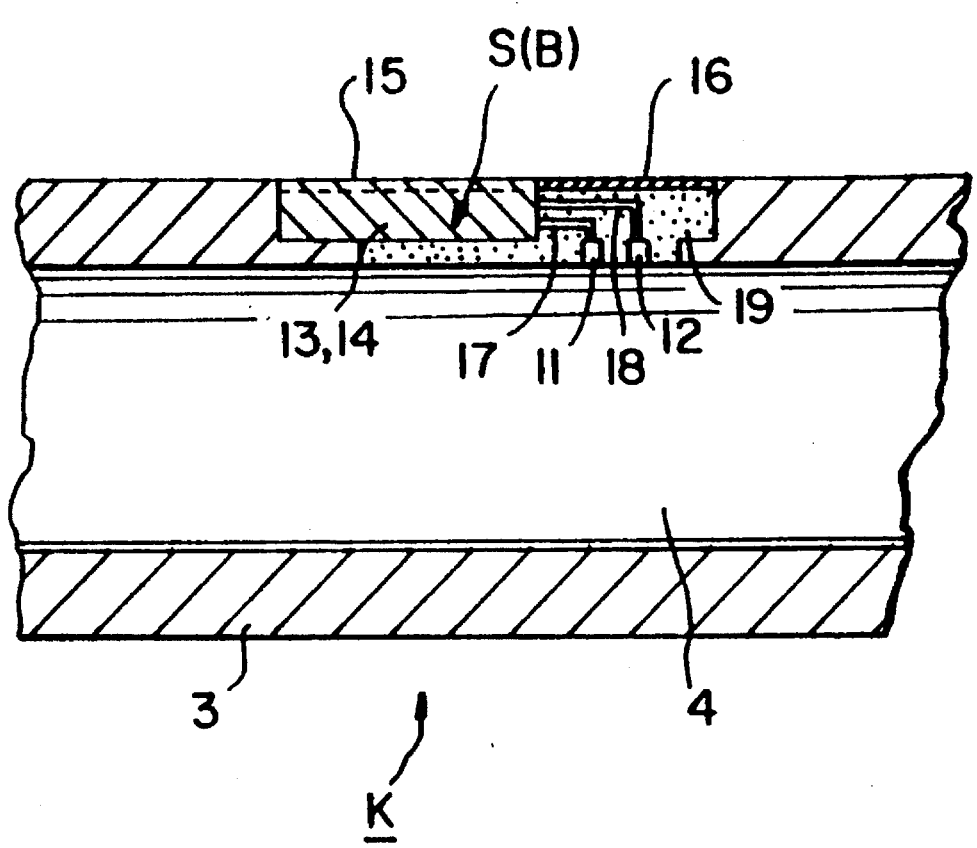
FIG. 4 is a view in section corresponding to FIG. 2 according to another embodiment of this invention.
Figure 3:
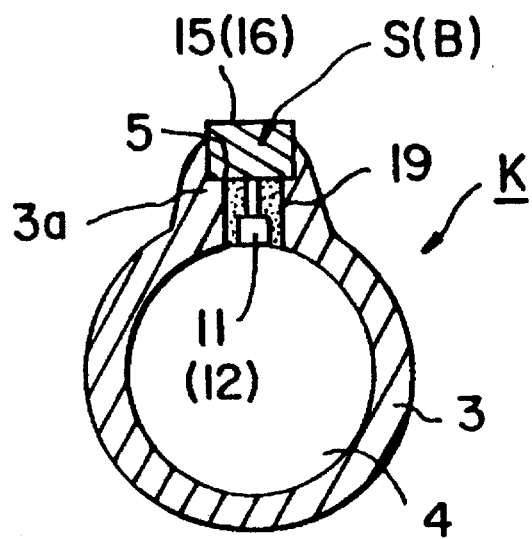
FIG. 3 is a view in section taken along line X3—X3 of FIG. 2.

FIG. 4 shows a second embodiment of the catheter K according to this invention, in which the same elements or similar elements are provided with the same reference numerals and symbols in order to avoid duplications of the description. In this second embodiment, the two control units 13 and 14 are made more compact than in the first embodiment by integrating them into a one electric circuitry and only a display device 15 is superimposed on the control units 13 and 14 in order to form a block unit B. A display device 16 is disposed in the position extending from the display device 15 or next thereto in a lengthwise direction. The sensors 11 and 12 are disposed below or under the display device 16 so as to come into touch with the fluids being passed through the fluid path of the catheter K. Further, the sensors 11 and 12 are connected with the control units 13 and 14 through lead wires 17 and 18, respectively. The control units 13 and 14 and the display device 15 may be formed in a block unit and the resultant block unit may in turn be integral with the display device 16. The resulting integral block unit may further be formed integrally with a synthetic resin portion 19, together with the sensors 11 and 12 as well as the lead wires 17 and 18. This integral block unit may be inserted or embedded into the mounting aperture or hole 19 of the tube wall 3 of the catheter K in substantially the same manner as in the first embodiment of the catheter according to this invention. More specifically, the integral block unit may be seated on a stepped seat portion of the mounting aperture or hole formed in the tube wall of the catheter K and it may be detachably incorporated into the tube wall of the catheter through a sealing member or integrally secured to the tube wall thereof with adhesive. The catheter K in this second embodiment according to the present invention can offer the advantage that the tube wall of the catheter K can be made thinner than that in the first embodiment.

As a power source for the functional elements 11 through 16, a small-size electric cell (a button-shaped electric cell) D may be employed and it may be incorporated into the catheter K, as shown in FIG. 2, in association with the functional elements. For example, as each of the sensors 11 and 12 to be utilized for the catheter K according to this invention may be of such a type as varying its resistance value in accordance with the temperature or pressure, the electric cell D may be employed in order to apply an electric voltage to the sensors 11 and 12 for sensing their resistance values. In addition, it may be employed for operating the control units 13 and 14 as well as the display devices 15 and 16.

As the electric cell D can be utilized for a considerably long period of time, it may be incorporated integrally into the block unit B in the stage of the production of the catheter K and it may be shipped with the detector unit S in an operative state. Further, the electric cell D may be incorporated into the catheter K on site from the outside, immediately before use, in order to avoid the operation of the detector unit S for an unnecessary period of time. In this case, for example, the block unit B may be provided with a section with or in which the cell D can be assembled or incorporated. In addition, for example, when the electric cell D is incorporated into the block unit B of the catheter K, a power switch may be mounted to the catheter K to start the operations of the cell D by turning it on immediately before the start of the cell D. The power switch may be of such a simple structure as being disposable once it has been utilized.

It is to be understood that the present invention is not interpreted as being restricted in any respect to the embodiments as described hereinabove and they are described simply for the purpose of illustrations and that this invention can encompass within its spirit and scope various modifications and variations as will be described hereinafter.

Such modifications and variations may include the features that follows.

1. The status of the fluids to be monitored may be only one of the temperature and pressure of the fluids being supplied to or drained from the body of a patient through the fluid passage 4.

2. The sensors 11 and 12 may be arranged so as to allow a majority of their parts to be embedded into the packaged block unit integral with the control units 13 and 14. On the other hand, the sensors 11 and 12, the control units 13 and 14 as well as the display devices 15 and 16 may be disposed in the catheter K in an appropriate distance apart from each other in its lengthwise direction.

3. The catheter K may be restricted to the purpose for supplying fluids to the body of a patient or for draining them therefrom and it may be of such a type as protecting the cardiac muscle or of a balloon type.

4. The data detected may be display in an analog type as well as in a digital type.

What is claimed is:

1. A catheter comprising:

a hollow tube having a tube wall forming a fluid passage therethrough;

at least one sensor mounted in the tube wall of the hollow tube of the catheter for sensing at least one parameter of a fluid passing through the fluid passage of the hollow tube of the catheter;

a display device having a data value indicator for displaying values of said at least one parameter of the fluid; wherein the display is mounted in the tube wall of the catheter with said data value indicator exposed externally of the tube wall thereof at a location enabling it to be visually monitored externally of a body of a patient into which the catheter is inserted;

a control unit, said control unit being connected to said at least one sensor for receiving output therefrom and being connected to said display device for providing said values of said at least one parameter to said display device;

an electric cell means for powering said at least one sensor, display device and control unit; and a block unit in which said control unit, the at least one sensor, the display device and the electric cell are integrally interconnected; wherein the block unit is embedded in the tube wall of the catheter.

2. The catheter of claim 1, wherein said at least one sensor is at least one of a temperature sensor and a pressure sensor.

3. The catheter of claim 1, wherein said at least one sensor is positioned in said tube wall exposed to fluid passing through said fluid passage; and wherein the block unit comprises a synthetic resin physically uniting the at least one sensor with the control unit and the display device.

4. The catheter of claim 3, wherein the tube wall of the catheter has an aperture forming a seat for said block unit, said aperture having first, radially outer portion in which said display device is located and an inner portion in which said synthetic resin is located; wherein said inner portion is circumferentially smaller than said outer portion; and wherein said at least one sensor is located in said inner portion within said synthetic resin.

5. The catheter of claim 1, wherein said at least one sensor is located laterally of the control unit; wherein said display device is plate-shaped; and wherein said display device is positioned above said at least one sensor.

6. The catheter of claim 1, wherein said at least one sensor is located laterally of the control unit; wherein said display device is plate-shaped; and wherein said display device is positioned above said control unit.

7. The catheter of claim 1, wherein said at least one sensor comprises a plurality of sensors; wherein a said control unit and a said display device is connected with each of said sensors; wherein all of the sensors, control units and display devices are physically united in said block unit; and wherein said display devices are positioned in a row extending in a lengthwise direction of the catheter at an outer side of the hollow tube.

* * * * *